(12) United States Patent
Serri et al.

(10) Patent No.: US 11,484,195 B2
(45) Date of Patent: Nov. 1, 2022

(54) AUTOMATED PERSONAL VISION TRACKER

(71) Applicants: John Serri, Newark, CA (US); Yue Wang, Newark, NJ (US); Noam Sapiens, Newark, CA (US)

(72) Inventors: John Serri, Newark, CA (US); Yue Wang, Newark, NJ (US); Noam Sapiens, Newark, CA (US)

(73) Assignee: EyeQue Inc., Newark, CA (US)

( * ) Notice: Subject to any disclaimer, the term of this patent is extended or adjusted under 35 U.S.C. 154(b) by 399 days.

(21) Appl. No.: 16/685,017

(22) Filed: Nov. 15, 2019

(65) Prior Publication Data

US 2020/0077886 A1   Mar. 12, 2020

Related U.S. Application Data

(63) Continuation-in-part of application No. 16/276,302, filed on Feb. 14, 2019, now Pat. No. 10,588,507, which is a continuation-in-part of application No. 15/491,557, filed on Apr. 19, 2017, now Pat. No. 10,206,566.

(60) Provisional application No. 62/767,731, filed on Nov. 15, 2018, provisional application No. 62/409,276, filed on Oct. 17, 2016.

(51) Int. Cl.
  *A61B 3/032* (2006.01)
  *A61B 3/00* (2006.01)
  *A61B 3/14* (2006.01)
  *A61B 3/103* (2006.01)

(52) U.S. Cl.
  CPC .......... *A61B 3/0325* (2013.01); *A61B 3/0033* (2013.01); *A61B 3/0058* (2013.01); *A61B 3/103* (2013.01); *A61B 3/14* (2013.01)

(58) Field of Classification Search
  CPC ... A61B 3/0325; A61B 3/0033; A61B 3/0058; A61B 3/103; A61B 3/14; A61B 3/10
  USPC .......................................................... 351/239
  See application file for complete search history.

(56) References Cited

U.S. PATENT DOCUMENTS

| | | | |
|---|---|---|---|
| 2013/0092816 A1* | 4/2013 | Barrett | G01J 9/00 250/201.9 |
| 2016/0242644 A1* | 8/2016 | Winsor | A61B 3/113 |
| 2019/0377236 A1* | 12/2019 | Jang | G02B 3/14 |

* cited by examiner

*Primary Examiner* — Mohammed A Hasan
(74) *Attorney, Agent, or Firm* — Steven A. Nielsen; www.NielsenPatents.com

(57) ABSTRACT

Disclosed embodiments may include a device, system and method for providing a low cost device that can measure refractive errors very accurately via attachment to a smart phone. A disclosed device may use ambient light or a light source in simulating the cross cylinder procedure that optometrists use by utilizing the inverse Shack-Hartman technique. Using an optical device, in conjunction with a smart phone, the user first changes the angle of the axis until he/she sees a cross pattern (the vertical and horizontal lines are equally spaced). The user adjusts the display, using motorized controls on the on the optical device, to make the lines come together and overlap, which corresponds to bringing the view into sharp focus, thus determining the appropriate optical prescription for the user.

8 Claims, 11 Drawing Sheets

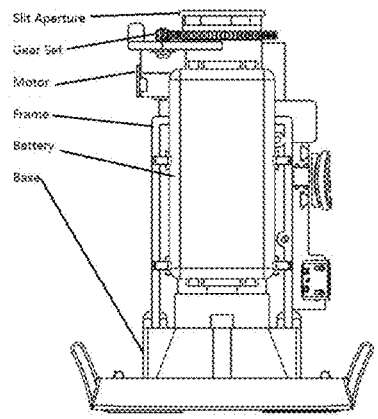
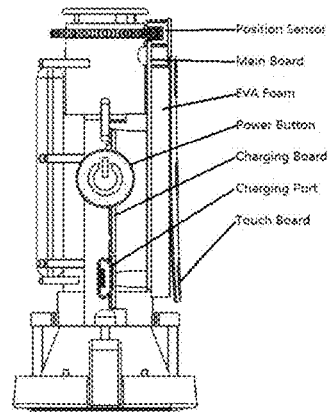
FIG 2.a.  FIG 2.b.
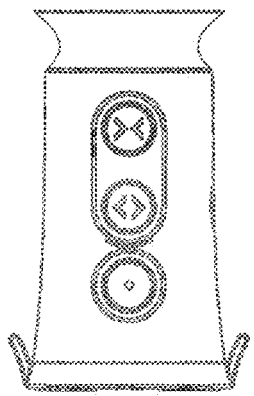
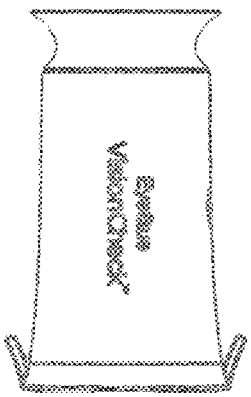
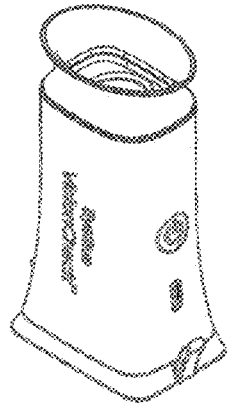
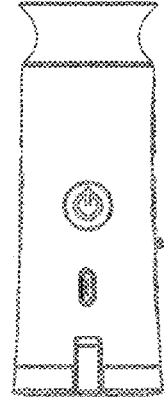
FIG 2.c.  FIG 2.d.  FIG 2.e.  FIG 2.f.
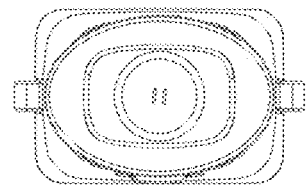
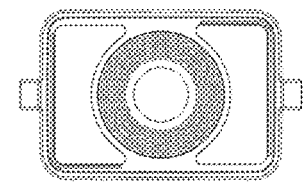
FIG 2.g.  FIG 2.h.

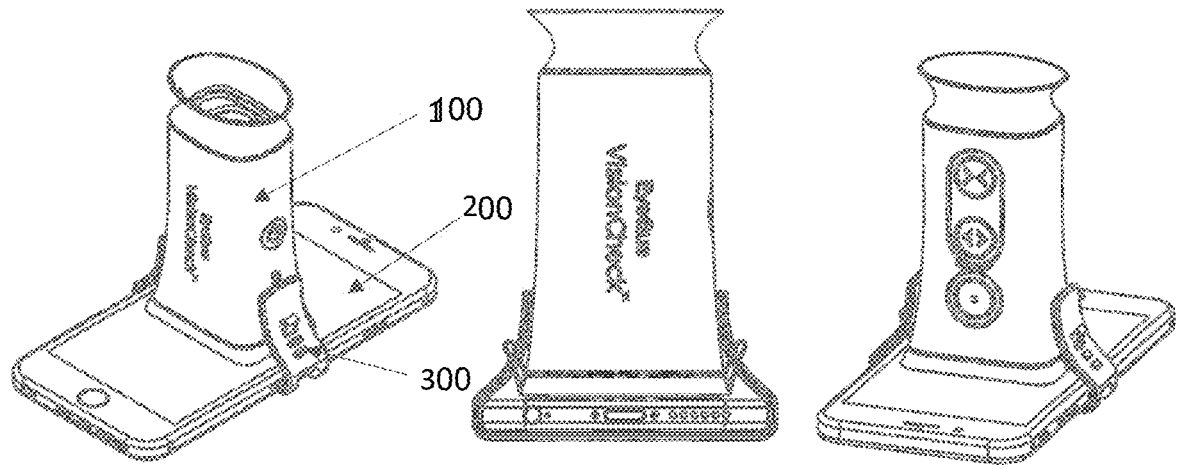
FIG 3.a.   FIG 3.b.   FIG 3.c.
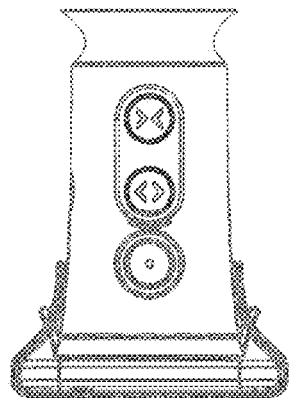 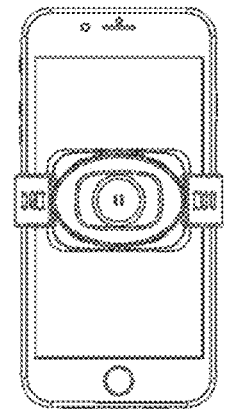
FIG 3.d.   FIG 3.e.

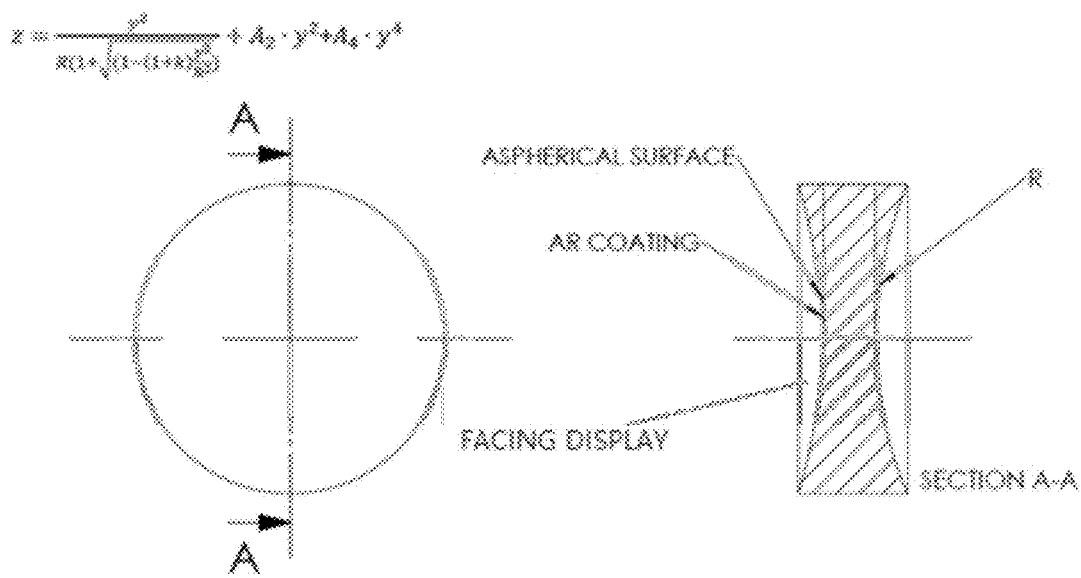
FIG 6.a.
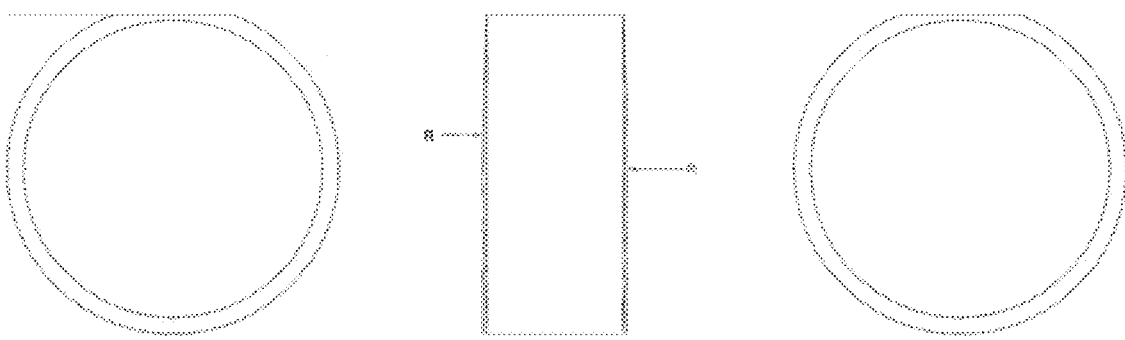
FIG 6.b.
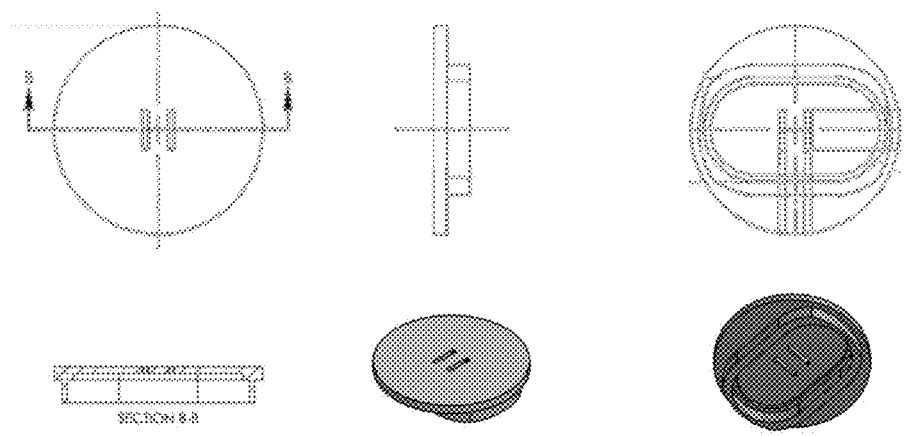
FIG 6.c.

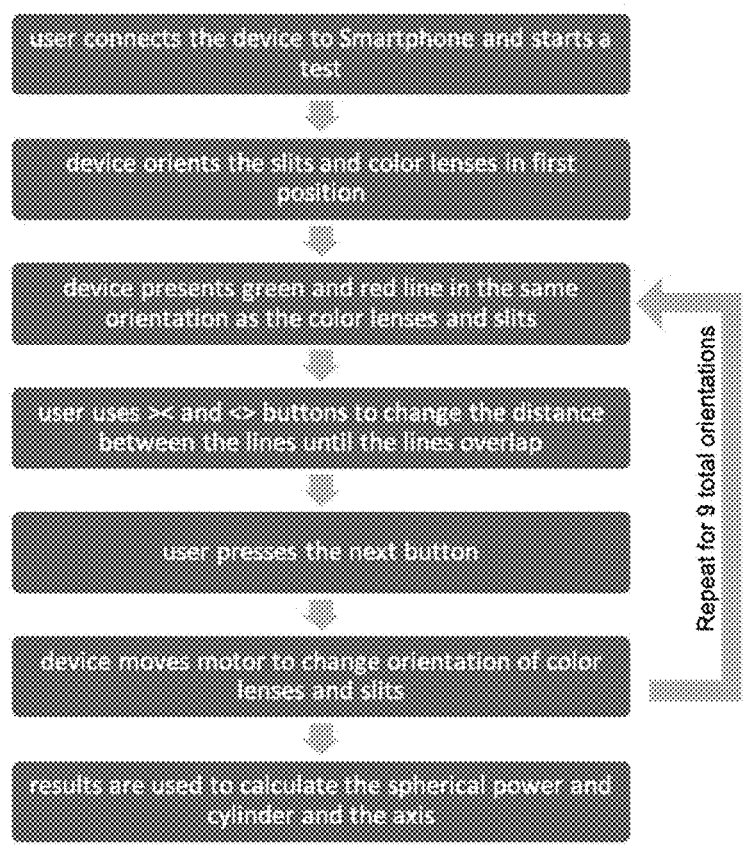
FIG 9.
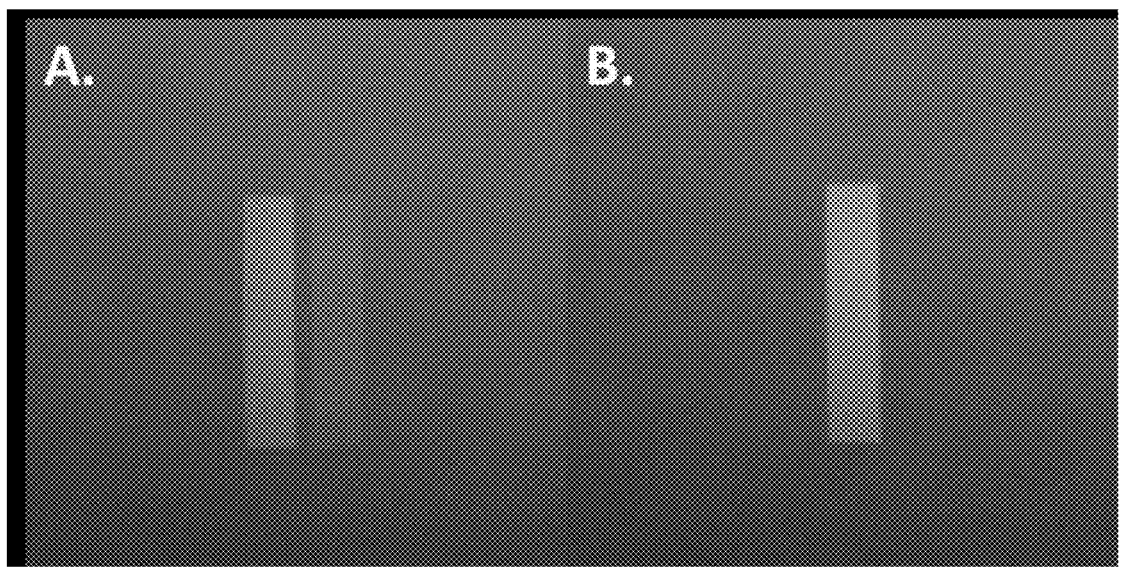
FIG 10.a.    FIG 10.b.

AUTOMATED PERSONAL VISION TRACKER

CROSS-REFERENCE TO RELATED APPLICATIONS

This utility application claims the benefit and priority of provisional patent application 62/767,731 filed on Nov. 15, 2018. This application is a CIP or continuation in part of utility application Ser. No. 16/276,302 filed on Feb. 14, 2019 which is a CIP of utility application Ser. No. 15/491,557 filed on Apr. 19, 2017, now U.S. Pat. No. 10,206,566 issued on Feb. 19, 2019, wherein the Ser. No. 15/491,557 application claims the benefit and priority of provisional patent application 62/409,276 filed on Oct. 17, 2016.

COPYRIGHT AND TRADEMARK NOTICE

This application includes material which is subject or may be subject to copyright and/or trademark protection. The copyright and trademark owner(s) has no objection to the facsimile reproduction by any of the patent disclosure, as it appears in the Patent and Trademark Office files or records, but otherwise reserves all copyright and trademark rights whatsoever.

BACKGROUND OF THE INVENTION

(1) Field of the Invention

The invention generally relates to vision testing systems. More particularly, the invention relates to means and methods of obtaining refraction information of an optical system using a refracting optical scope used to observe and manipulate line patterns generated upon the screen of a smart phone.

(2) Description of the Related Art

The known related art fails to anticipate or disclose the principles of the present invention.

In the related art, U.S. Pat. No. 8,783,871 by Pamplona et al discloses general methods of finding refraction values using a generalized Shack-Harmann technique. However, the Pamplona patent fails to disclose efficient and economical means of leveraging the current high density pixel pattern of today's smart phones.

In the related art, consumers, as a practical matter, are still, for the most part, spending inordinate amounts of time and money to obtain refractions from traditional brick and mortar optometry offices.

Thus, there is a long felt need in the art for the present invention.

GENERAL BACKGROUND

Vision is arguably the most important of the senses. The human eye and its direct connection to the human brain is an extremely advanced optical system. Light from the environment goes through the eye optical train comprised of the cornea, the pupil, and the lens and focuses to create an image on the retina. As all optical systems, light propagation through the eye optics is subject to aberrations. The most common forms of aberrations in the eye are defocus and astigmatism. These low order aberrations are the cause of the most common refractive eye conditions myopia (near-sightedness) and hyperopia (farsightedness). Higher order aberrations are also present and can be described most conveniently by the Zernike polynomials. These usually have a lower effect on visual function. The eye, like any other organ in the human body, may suffer from various diseases and disorders, the most prominent today are: cataract, AMD, glaucoma, diabetic retinopathy, dry eye.

Ophthalmic measurements are critical for eye health and proper vision. Those ophthalmic measurements could be sectioned into objective and subjective types. Objective types measurements give a metric of a physiological, physical (e.g. mechanical or optical), biological or functional without the need for input from the measured individual (patient, subject, user or consumer). Examples of objective tests include but are not limited to OCT (optical coherent tomography used to image a 3 dimensional and cross sections of the eye), scanning laser ophthalmoscope (SLO, used for spectral imaging of the retina), fundus image (used to present an image of the retina), auto-refractor (used for refraction measurement), keratometer (used for providing a profile of the cornea), tonometer (used to measure the IOP—intra ocular pressure). Subjective measurements give a metric with relation to the individual input. That is, they provide parameters that also take into consideration the brain functions, perception and cognitive abilities of the individual. Examples of subjective tests include but are not limited to visual acuity test, contrast sensitivity test, phoropter refraction test, color vision test, visual field test, and the EyeQue PVT and Insight.

Today, both objective and subjective eye exams (measurements) are done by an ophthalmologist or an optometrist. The process usually involves the patient needing to schedule an appointment, wait for the appointment, travel to the appointment location (e.g., office or clinic), wait in line, perform multiple tests using various tools and potentially moving between different technicians and different eye doctors. The prolonged wait times both for the appointment as well as in line at the appointment location, along with the hassle of performing the tests with different professionals and the duration of those tests might seem daunting to many patients. Furthermore, the shear effort associated with the process and even the requirement of remembering to start the process to begin with might deter patients from going through with a traditional examination.

Moreover, currently about 2.5 billion people do not have access to eye and vision care at all. The cost of eye exams could be considered quite significant especially in some places in the world. This poses a hindrance to the availability of eye care in third world countries for example. The cost, time consumption and perceived hassle also makes it at times prohibitive to have repeated eye exams, especially at the desired frequency. Those might be necessary in special cases (for example after refractive surgery or cataract surgery where repeated measurements should be performed to track the progress of the patient's status over time and the success of the surgery. Additionally, even under normal circumstances, measurements at a doctor's office only represent a single point in time. The situation under which the measurements were made might not be optimal or do not fully represent the patient's characteristics. The patient might have been tired, stressed or agitated (a doctor's visit might be quite stressful in and of itself but could also being run from test to test and being posed with questions and options elevate the patient's level of stress) or was just in a bad mood. Even the state of mind of the doctor themselves might influence the way the measurement is performed. Beyond all that, the time of day and other environmental conditions (whether direct e.g. lighting conditions or indirect e.g. temperature) could also affect the measurement and provide incomplete or false information.

The availability of information (including specifically medical information) on the Internet, the increased awareness of people for preventive medicine, and the emergence of tele-medicine leads to many taking control of their own health. Devices for screening, monitoring and tracking medical conditions are quite pervasive in today's world, for example blood pressure measurement devices, and blood sugar monitors. The technological advancements allow for people to be more independent in diagnosis, prevention and tracking of various health conditions. Furthermore, many prefer to perform these activities in the comfort of their homes without the need for appointments or other time-consuming activities. In case of an anomaly, they would call or email their physicians to consult for the appropriate course of action.

The advancement of technologies effectively makes computers with screens and cameras ubiquitous in the form of laptops, tablets and smartphones. Therefore, enabling many people to have a device already capable of computing displaying and recording information.

All this brings the need for a series of devices that will enable users to perform ophthalmic measurements at home, by themselves, in a timely and cost-effective manner. It should be clear that the quality of these measurements and their accuracy and precision should meet or exceed the standards of today's measurement methods.

This vision could be further enhanced by use of cloud-based data and analytics that enables complete access to the entire history of a patient exams, tests and measurements. Moreover, the use of artificial intelligence (AI) will enable diagnosis based on machine learning and big data. This could be done by means of data mining, neural network decision making and pattern detection and recognition, as some examples of the AI capabilities.

To summarize, the vision for eye care in the not so far future will look like:
  A complete solution for eye and vision care for consumers and doctors.
  Remote, self-administered battery of tests for both disease and functional measurements are enabled by technology and devices
  AI is used for analysis, tracking and reporting. Enhanced by big data correlations and insights In simple terms, as an example: A person sits on their couch at the comfort of their home, uses a device to do various measurements, that data is uploaded to an AI for analysis. The AI will let the person know the results and notify the doctor. The AI will initiate alerts for the person and doctor in necessary cases. The person will not need to get up unless a serious issue occurs (i.e. surgery). All other issues will be dealt with remotely (e.g. email/phone/video conference with the doctor, order glasses and have them delivered to the home, direct delivery of doctor prescribed medications).

Despite the apparent approach of "direct to consumer", the methodologies could easily be implemented for a more enterprise like model. One example of such implementation will have a hierarchical structure in which an entity such as a hospital, association, or a medical insurance company provides the ability for the doctors to provide their patients with such devices and capabilities. The devices are all connected through the user accounts to the cloud and the measurements are streamed directly into the users' accounts (and potentially their medical records). Those accounts could be attached to one or more doctors and can also be transferred and shared.

BRIEF SUMMARY OF THE INVENTION

The present invention overcomes shortfalls in the related art by presenting an unobvious and unique combination and configuration of methods and components to create an apparatus that may be attached to a smart phone, with the apparatus presenting lines or other markings generated by the smart phone. An end user looks through the apparatus, makes adjustments to the presented markings and causes internal parts of the apparatus to rotate. A measurement is done on the markings at different rotations and is used to derive the end user's eyeglass prescription. A wireless or Bluetooth interface may be used to change patterns presented on the phone screen based upon control commands from the scope device or other disclosed embodiment.

The invention overcomes shortfalls in the related art by using colored lenses, a new system of using an aspheric lens as a demagnifying lens, a lens closest to the screen of the smart phone, the use of one moving part, a rotational gear, driven by a stepper motor, Bluetooth interface for screen control and other components and systems as described herein. The rotational gear and related configurations overcome shortfalls in the prior art as the rotational gear mount may contain two lenses and slits attached to an eyecup. A gear mount may be driven by a stepper motor with a pinion on an output shaft, the output shaft may be disposed upon the gear mount. Gears and other components may be driven by other devices such as PCB motors.

Embodiments of the invention may be described as a refracting optical scope used to observe line patterns on a smart phone. A disclosed device may have a length of about 100 mm and the radius about 50 mm. But, other sizes and configurations are contemplated and disclosed herein, and the disclosed embodiments are not limited to any size. Components may comprise three lenses and two slits. To measure the amount of spherical asymmetry in an optical component under test, wherein an "optical component" could include the human eye, the slits and upper lens assembly rotate about different angles in the plane perpendicular to the optical axis of the device. Electrical elements may comprise a Li-Ion battery, LEDs, PCB boards, Bluetooth interface, Stepper Motor, Touch Sensor, Haptic Motor and Light sensor.

Disclosed embodiments may attach to a smart screen surface using a variety of means, including micro suction tape and/or band or other holders to secure and align the device to the phone.

Disclosed embodiments may interact with a smart phone by use of a Bluetooth connection or other means of wireless communication. By use of a plurality of user controls, such as touch buttons, a user is able to adjust or vary the distance, d, between two parallel red and green images illuminating from a smart phone display. The user controls may also be used to move the red and green images closer or farther to each other or to rotate the images as well as advancing the rotational slits to the next angle. When the user touches the rotation button it rotates the lines on the screen and will also advance the rotational slits on the device by the same amount. The movement of the slits is accomplished by use of a stepper motor geared to the slits. Each angle movement may be a 40 degrees clockwise rotation.

User controls may have a haptic vibration when pressed. When touched, a user may perceive a slight vibration originating from a haptic motor to provide user feedback. The controls support both long touch and short touch commands. To avoid accidental advances in angle, a rotate command is sometimes carried out in response to a long touch only, and only after the distances between the patterns on the phone have had their distance changed.

These and other objects and advantages will be made apparent when considering the following detailed specification when taken in conjunction with the drawings.

BRIEF DESCRIPTION OF THE DRAWINGS

FIG. 2. a-h. present different detailed views of a proposed embodiment of the invention.

FIG. 3. a-e. present illustrations of an embodiment of the proposed invention attached to a smartphone by a universal rubber band.

FIG. 6. a-c. present examples of proposed designs of the main elements in the optical train of an embodiment of the invention.

FIG. 9. presents a flow diagram of a measurement method in an embodiment of the invention.

FIG. 10. a-b. present images that a user may see while using the invention.

Figure 1:
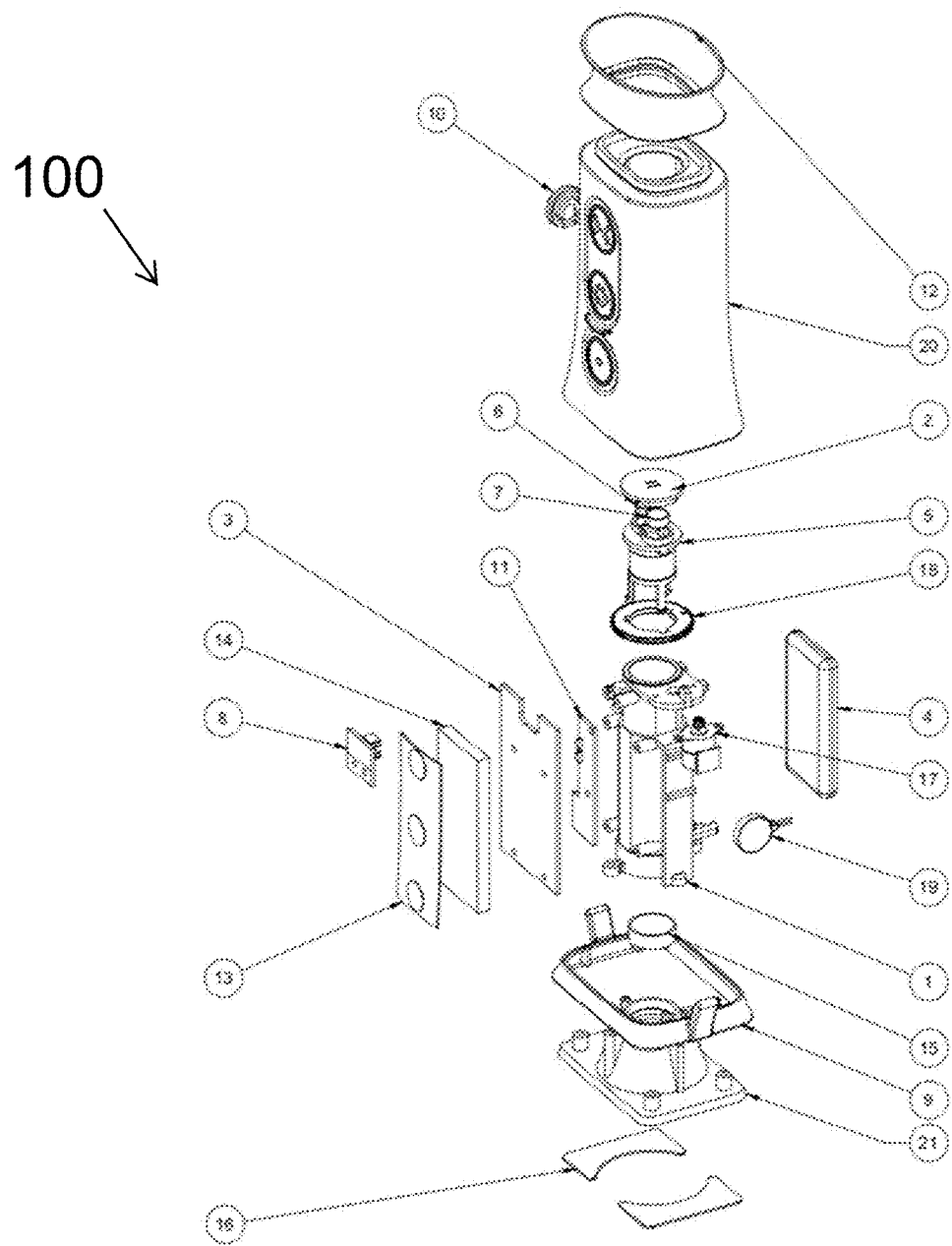
FIG. 1. presents a blown-up illustration of an embodiment of the invention.

REFERENCE NUMERALS IN THE DRAWINGS 1 main body
2 slits or voids
3 main board
4 battery
5 bearing
6 green lens
7 red lens
8 home sensor
9 hooks
10 on/off button
11 charging board
12 eyecup
13 touch buttons
14 foam pad
15 aspheric lens
16 tape
17 stepper motor
18 rotation gear
20 cover
21 base body
100 a disclosed embodiment
200 smart phone
300 strap

DETAILED DESCRIPTION OF EMBODIMENTS OF THE INVENTION

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

Any and all the above references and U.S. patents and applications are incorporated herein by reference. Aspects of the invention can be modified, if necessary, to employ the systems, functions and concepts of the various patents and applications described above to provide yet further embodiments of the invention.

An embodiment of the invention apparatus is presented in FIG. 1 in a blown-up mechanical drawing. Markings indicate different components of the apparatus. The components in the design could be partitioned into three main parts: the optical components of the device (the aspheric lens (15), the green lens (6), the red lens (7) and the slits (2)), the electronic components of the device (the battery (4), the stepper motor (17), the haptic motor (19), the touch buttons (13), the home sensor (8), the main board (3) and the charging board (11)) and the mechanical components (the eyecup (12), the cover (20), the bearing (5) the rotation gear (18), the main body (1), the hooks (9), the base body (21), the micro suction tape (16), the foam pad (14) and the on/off button (10).

A more detailed view of a proposed embodiment of the invention apparatus is presented in FIGS. 2.*a-h*. In general, the optical components allow for an image to be presented to a user in a way to enable the measurement of refraction properties of an optical system. In one embodiment the images are presented to a user and the refraction measurement is done on the user's eye. The electronic components allow for user control of various aspects of the invention, for example, the rotation angle of some component within the apparatus or some aspect of the presented images, thus allowing a self administered refraction measurement. The mechanical components are used to secure components together, while at the same time allowing for the required motion of various parts. It also enables the required system alignment.

A detailed description of components and rationale of potential embodiments of the apparatus of the invention is hereby presented:

Optical components: aspheric lens (15) is used to diverge the smart phone screen image and provide demagnification to increase system resolution, the aspheric aspect of it is introduced to reduce aberrations and distortion in the system, as a spherical lens introduces enough of those to make the presented lines on the display seem curved to the user despite being straight; the green lens (6) and the red lens (7) are used in the demagnification process as well as separate the image according to the transmission of the different colors to prevent cross talk between the image transfer of the green and red lines displayed on the screen, this is the basis of the reverse Shack-Hartman technology to measure the refraction of the measured system, as the light travels through two different optical paths in the device; the slits (2) are used to reduce the field of view of the images to allow only for a portion of the light to go through and avoid crosstalk before the focus in the measured system.

Electronic components: battery (4) used to power the device and provide the driving current to the various electronic components, alternative forms of energy sources may be considered; stepper motor (17) used to control the rotation angle of the color lens pair and slits, alternative motion control could be entertained: PCB motors, servo motors, piezo-electric motors, voice coils; haptic motor (19) is used to provide response to the user as indication of pressing one of the buttons; touch buttons (13) are used to control the device—move the lines closer or farther and change the rotation angle; the home sensor (8)—is used in conjunction with counting steps to determine the absolute angle of the color lens pair and slits, alternatively, position sensors, encoders (optical, magnetic or mechanical) may be implemented to determine the absolute angle of the color lenses and slits; main board (3) holds the complete functionality of the device and includes (but not limited to): quality metrics on the device, motor controller, logic of operation, firmware, Bluetooth connectivity to the smartphone, input from the buttons; charging board (11) includes the circuitry to perform charging of the battery, a USB connector (11*a*) as the input power source for the charging, battery level measurement and indicators, the on/off button (10) and indicator LEDs. Disclosed embodiments may include a myriad of controls such as voice commands or various device controls such as those sometimes used by video gamers.

Mechanical components: eyecup (12) used to allow a user to attach their eye to the device and protect it from harm, it also allows some control of the distance of the device from the user's eye, which is an important distance needed for proper calibration of the device; the cover (20) presents the company logo, the location of the buttons and covers the internals of the device from the user, it also serves as an aesthetic feature of the device; the bearing (5) and the rotation gear (18) serve as transmission from the motor to the color lens pair and slits to enable the required resolution of the rotation angle; the main body (1) and the base body (21) are used to hold the optics in place and serve as the required alignment between the optical components; the hooks (9) are used for connecting the rubber band that connects the device to the smartphone; the micro suction tape (16) is used to adhere the device with out use of chemical adhesive to the smart phone screen and prevent it from slipping and sliding, it is made such as to not leave any residue or mark on the display; the foam pad (14) is used to isolate the touch buttons from the main board and to press the buttons against the cover to create good touch sensitivity.

The proposed apparatus could be attached to a display for presenting the measurement images. This display could be a smartphone as seen in FIGS. 3.*a-e*. The device is attached to the smartphone using a universal rubber band that allows attaching it to any smartphone. The device has features, for example (9) in FIG. 1 that allow for the attachment of the rubber band.

Figure 4:
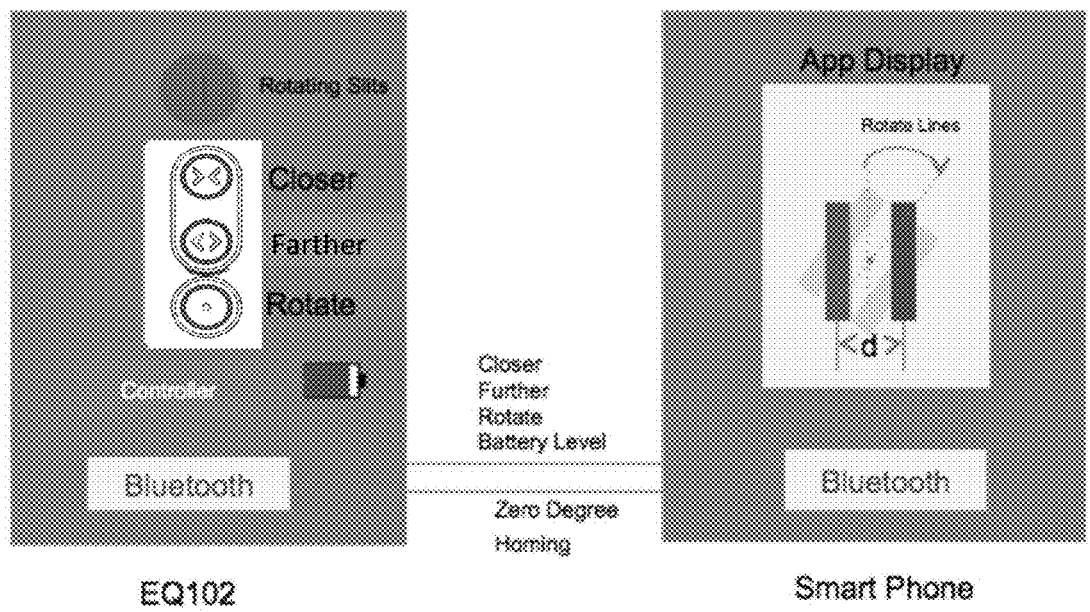
FIG. 4. presents a functional block diagram of an embodiment of the invention.

In an embodiment of the apparatus of the invention, the electronic components work together to enable the performance of the refraction measurement of the measured system. A functional block diagram of an embodiment of the invention is presented in FIG. 4. The left part represent the functionality of a proposed apparatus of the invention, while the right side presents a smartphone interface with the apparatus. The device functionality includes the physical rotation of the color lens pair and the slits using a motor, the button user interface to control the distance between the lines on the smartphone display and to progress the measurement between the angles of rotation, together with a haptic motor to provide the user with touch button feedback, the power source or battery, a controller and driver that integrate the logic and functionality of the apparatus and connect through Bluetooth to the smartphone. The smartphone functionality includes the display of the lines, the logic of the measurement procedure, the calculation of the measurement metrics such as eye glass numbers (spherical power, cylinder and axis) WiFi/cellular cloud connectivity to allow for these calculations to be done on the backend, a processor to run the app and a Bluetooth connection to the device. The connection between the device and the smartphone relays commands and information that include the zero degree homing and rotation motion of the motor, the motion of the lines, and the battery level for example.

Figure 5:
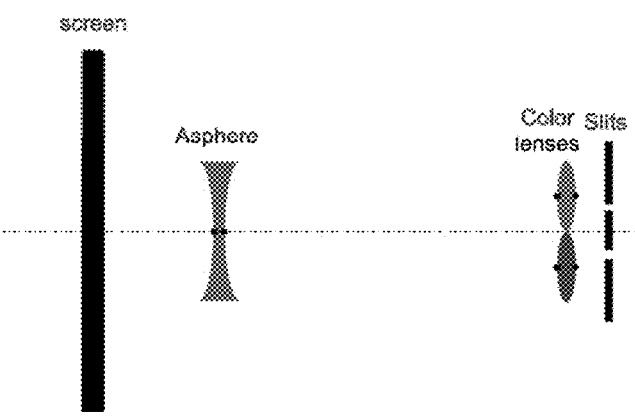
FIG. 5. presents a schematic illustration of the optical train in an embodiment of the proposed invention.
Figure 7:
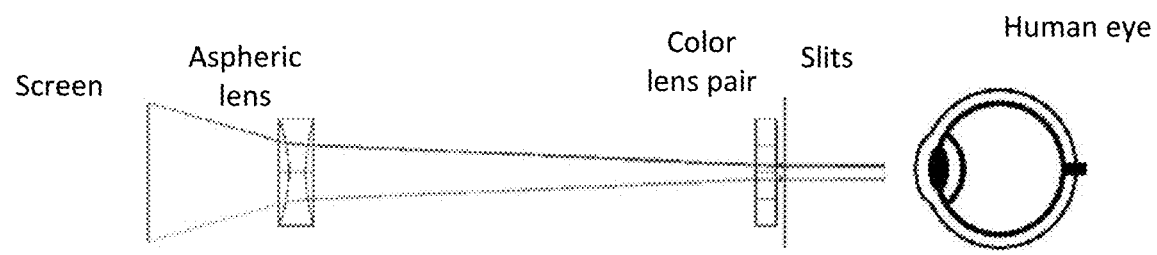
FIG. 7. presents a ray tracing analysis of an embodiment of the invention.

An embodiment of the optical train of the invention apparatus is presented in FIG. 5. Light emanating from a display (screen) travels through a demagnifying lens (asphere). That lens might be a negative power lens, an aspheric lens as depicted in FIG. 6.*a*. or other diverging optical mechanism. The light then travels to a pair of color lenses. One lens is colored red (bottom of color lenses) allowing only red wavelengths to pass through, blocking all other wavelengths. Another lens is colored green (top of color lenses), allowing only green wavelengths to go through, preventing all other colors from passing. This segmentation in color/wavelength, allows presentation of different colors on the display to pass through h different optical paths in the system. That in turn is the basis of the technological foundation of the device. The lenses in the pair are identical and an example for the design is given in FIG. 6.*b*. Light from the lens pair then travels through two slits (slits in FIG. 5), one against each lens. An example design of the slits is presented in FIG. 6.*c*. The slits are used to separate the images and prevent cross-talk between the red and green images before entering the measured optical system. The slit spacing is such to allow both the red and green images to enter the pupil of the eye. A ray trace analysis of the above description is presented in FIG. 7, showing the propagation of a red (top) and green (bottom) features on the display through a proposed embodiment of the invention apparatus. FIG. 7 also presents a model of the human eye (Human eye model) and the trace of the rays of the red and green images into the eye.

Figure 8:
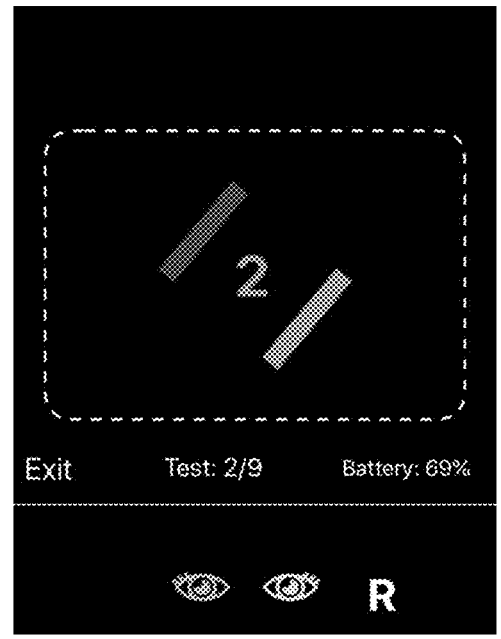
FIG. 8. presents an example of a screen of an application on a smartphone used in the implementation of the invention.

In an example of an embodiment of the invention the image presented on the display is of two lines, one red and one green. The image is oriented in the same rotational direction as the color lens pair and the slits. The distance between the lines is a measure used in the determination of the refraction of the system under test. FIG. 8 presents such example embodiment. The image could be a part of a smartphone application (app). In an embodiment of the invention the refraction measurement procedure is presented in FIG. 9. After the user connects the device to the smartphone via Bluetooth and starts the test, the device orients the slits and color lens pair to the first position. The smartphone presents a green line and a red line on the display at the same orientation as the slits and color lens pair. The user can then modify the distance between the lines by pressing one of the two buttons on the device. While the user is looking through the device at the smartphone display, they will see an image corresponding to that in FIG. 10.a. As they modify the distance, the user should try to make the lines overlap as seen in FIG. 10.b. When the measurement is of a human eye, the edge detection of the human eye and the color contrast between red and green is the most pronounced and thus enable quite accurate alignment in most cases. For an industrial system, for example, a camera can be used, and image processing based on the centroid detection of the lines or on edge detection can determine when the lines overlap. The user then presses the next button and the distance between the lines is recorded for that particular rotation angle. The device then moves the motor to change the angle of the color lens pair and slits. The process is repeated 9 time (for example) and the results are used to calculate the eye glass numbers. Other forms of calculations may be done in the back end, including for example, averaging and bad measurement elimination. The analysis could follow a simple curve fitting algorithm to match to the following formula:

$$P = S + C \sin^2(a-\theta)$$

Where P is the measured power (converted through calibration from the pixel distance recorded from each rotation), S is the spherical power, C is the cylindrical power, a is the cylinder axis and θ is the different rotation angles.

The testing, validation and calibration of some of the proposed embodiments of the invention are crucial for the correct, accurate, repeatable and reliable implementation of the invention. One aspect is the motor operation, while another is the optical performance of the device.

Figure 11:
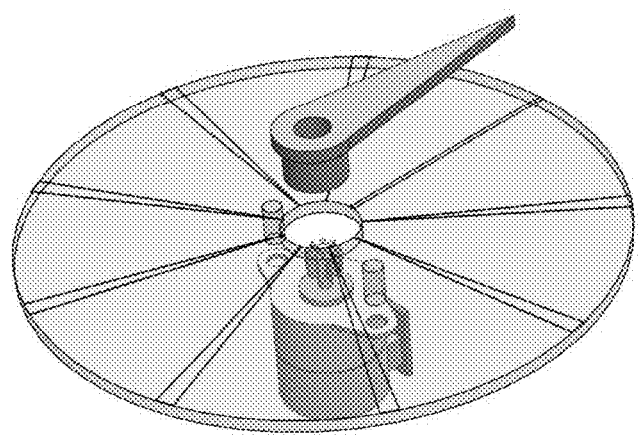
FIG. 11. presents a device used in the test and calibration of the motor used in an embodiment of the invention.
Figure 12:
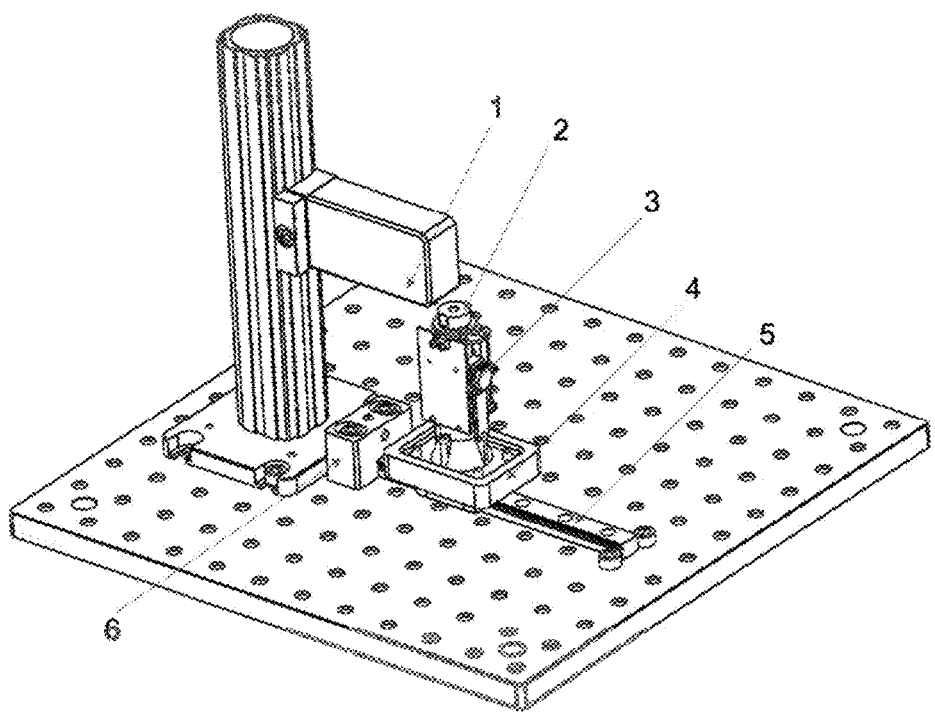
FIG. 12. presents a setup used in the test and calibration of the rotation feature in the invention.

The device depicted in FIG. 11 may be used to measure the repeatability and reliability of the motor in an embodiment of the invention. The motor is attached to a dial placed on a marked disk. The marking on the disk correspond to acceptable angle tolerances for each measurement rotation angle. The motor is then controlled and rotated between the different angle to validate performance.

A more general approach, to include the tolerances in the construction of an embodiment of the invention, for example the gear transmission of the rotation and the structural alignment of the device, is presented in FIG. 11. In this figure the measurement is not limited to just the motor performance but rather looks at the device as a whole and enables repeatability and reliability of the rotation feature of the device in a wholistic approach. The device (3) is placed in a special holder (4) on a rail (5) that allows it to be move to a position and maintained there by an alignment barrier and a magnet (6). A cap with a magnet in its center (2) is placed on the device instead of the slits. As the device slides in its place it s aligned under a magnetic encoder (1). Rotation of the device is then carried using the device controls and the encoder readings are recorded. The recorded data is then compared to the tolerance specs of the device. Variation of this method and apparatus include for example, other alignment mechanisms, other types of encoders and even built in encoders.

Figure 13:
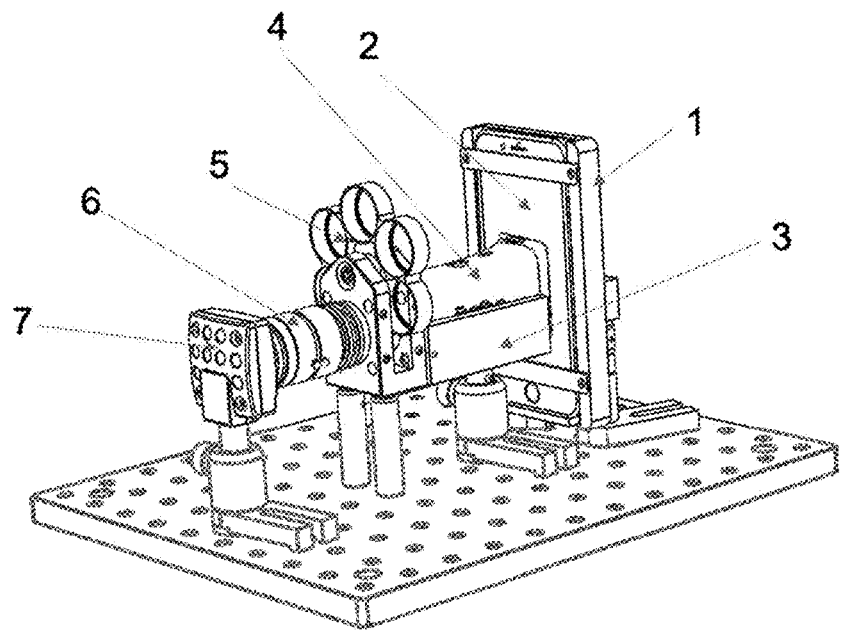
FIG. 13. presents a setup used in an optical calibration of an embodiment of the invention.
Figure 14:
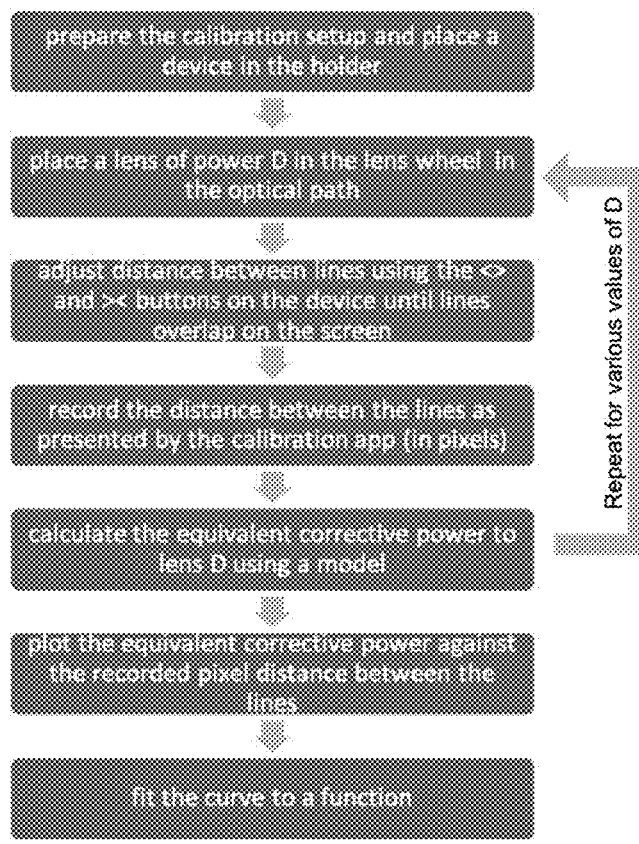
FIG. 14. presents a flow diagram of a calibration process of an embodiment of the invention.

In an embodiment of the invention an optical calibration is required. This calibration enables mapping of a measured property to a refraction metric. An example of a measured property is the distance between the lines in FIG. 8 that could be measured in pixels. Examples of a refraction metrics are spherical, cylindrical and axis ophthalmic correction factor values of a human eye. The calibration setup in FIG. 13 allows for such mapping between the pixel distance of the two lines presented in FIG. 8 and the equivalent spherical equivalent corrective power of the human eye. The calibration setup is thus comprised of a smartphone holder (1) holding a smartphone (2). An embodiment of the apparatus of the invention (4) placed in a special holder (3) to allow for robustness, stability and repeatability between different device placements. A lens wheel holding lenses of various power values (5), for example 10 lenses in the range between −10D and 10D. A camera (7) connected to a camera lens (6) that is adjusted to infinity. The system is aligned to allow viewing of the smartphone images through the device, the lenses of the lens wheel and the camera lens on the camera in the optimal fashion. This includes parameters such as image quality, centration, angular alignment, to name a few. Alternative builds of this setup could be constructed including mechanical variations and automation (e.g. the lens wheel). The calibration procedure in that case is presented in FIG. 14: A lens of power D is placed in the optical path, in the lens wheel. The distance between the lines is adjusted using the app on the smartphone until the lines overlap in the image taken by the camera.

Noam to add a diopter equation for the system based on PPI, distance between lines, demagnification factor, etc This could be achieved by an operator estimate or by image processing. The distance between the lines is then recorded against the lens power. The equivalent corrective power is calculated using a model, for example by a computerized ray tracing software. The process is repeated for all lenses in the lens wheel. The results are plotted as the equivalent corrective power vs. the pixel distance between the lines. The curve is then fit to a polynomial (e.g. a second order or a fourth order polynomial). For a second order polynomial the formula is given by:

$$P = a(d - d_{0D}) + b(d - d_{0D})^2$$

Where P is the equivalent corrective power, a is the linear coefficient, d is the distance between the lines in pixels, $d_{0D}$ is the distance between the pixels for 0D or no lens and b is the quadratic coefficient.

The fit could then be used in a more general way for other smartphones depending on their PPI according to the following formula:

$$P = a\left(\frac{PPI_{ref}}{PPI}\right)\left(d - d_{0D}\left(\frac{PPI}{PPI_{ref}}\right)\right) + b\left(\frac{PPI_{ref}}{PPI}\right)^2\left(d - d_{0D}\left(\frac{PPI}{PPI_{ref}}\right)\right)^2$$

Where PPI is the points per inch of the smartphone used for the measurement and $PPI_{ref}$ is the point per inch of the smartphone used in the calibration.

Figure 15:
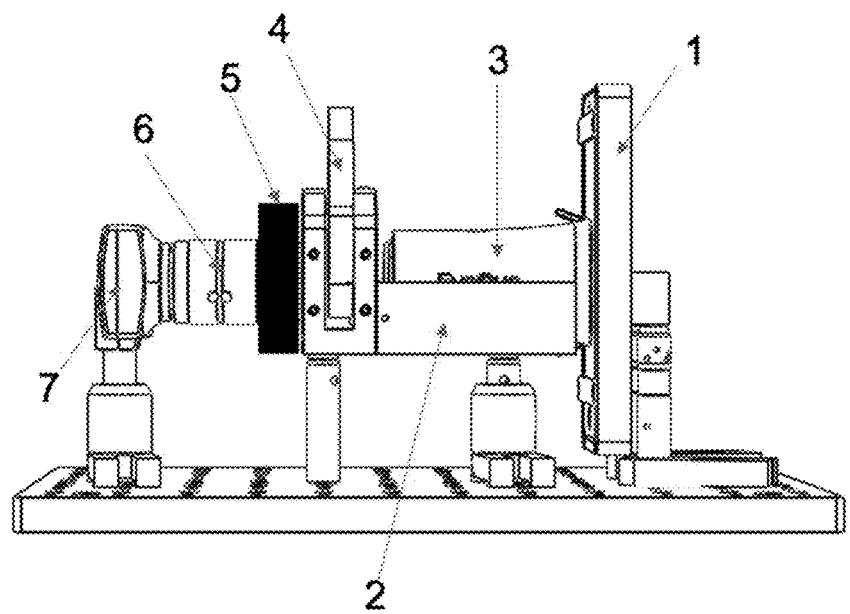
FIG. 15. presents an alternative setup used in the optical calibration of an embodiment of the invention.

An alternative methodology that does not depend on simulation of an embodiment of the invention, the calibration setup and the measured system is presented in FIG. 15, in which a variable lens is implemented in the optical train of the system. The rest of the calibration system follows the description of FIG. 13. The variable lens is a lens that its focal length could be modified. In one embodiment this variable lens is a membrane encompassing a liquid with change controlled by the amount of liquid present within the membrane part exposed in the optical path. The control mechanism may be piezoelectric, where a piston mechanism or similar controls the amount of liquid in the membrane and thus its shape. Alternatively, the control mechanism may be electrostatic with the same mechanism for changing the shape of the lens and thus its focal length. Another embodiment may include a set of two lenses where the distance between them may be adjusted to control the effective focal length of the pair, by the following formula:

$$\frac{1}{f} = \frac{1}{f_1} + \frac{1}{f_2} - \frac{d}{f_1 f_2}$$

Where f is the effective focal length of the pair, $f_1$ and $f_2$ are focal lengths of the two lenses and d is the distance between the lenses.

Figure 16:
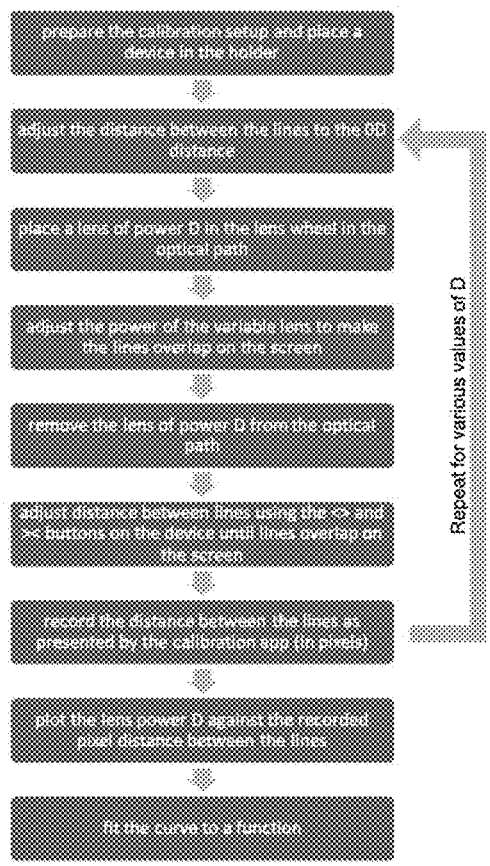
FIG. 16. presents a flow diagram of an alternative calibration process of an embodiment of the invention.
Figure 17:
FIG. 17 depicts a disclosed embedment in use

In FIG. 15 the variable lens is placed between an embodiment of the invention apparatus and the camera focus lens. In an alternative implementation, the variable lens may be placed between the camera lens and the camera. The calibration procedure in this methodology follows FIG. 16. In this case the first step is to find the 0D pixel distance according to the same methodology as for the first setup. A lens is then placed in the optical path. The power of the variable lens is then modified to align the lines measured in through the camera. At that point the lens from the lens wheel is removed (the power of the variable lens is maintained) and the lines are aligned using the controls on the device and the app. The distance between the lines is then recorded against the lens from the lens wheel power. This is repeated for all lenses in the lens wheel and the same procedure as before continues for the analysis.

The same generalization can be made in this case to match any smartphone PPI.

What is claimed is:

1. An optical device suitable for attachment to a smartphone, the optical device comprising:
   a) a first lens used for demagnification;
   b) a colored second lens and a colored third lens;
   c) a slit piece defining a first slit void within sight lines of the second lens and the slit piece defining a second slit void within sight lines of the third lens;
   d) user controls disposed upon an exterior surface of a housing, the user controls allowing a user to control a motor so as to rotate the slit piece along with the second and third lenses to align images presented by a screen of the smart phone.

2. The optical device of claim 1 wherein the first, second and third lens are mounted within a lens mount and wherein the lens mount is contained within a spur gear.

3. The optical device of claim 2 wherein the slit piece is disposed above the spur gear.

4. The optical device of claim 3 wherein a motor is in geared attachment to the spur gear.

5. The optical device of claim 4 further comprising housing containing the first, second and third lens, the spur gear and the slit piece.

6. An optical device suitable for attachment to a smartphone, the optical device comprising:
   a) a first lens used for demagnification;
   b) a colored second lens and a colored third lens;
   c) a slit piece defining a first slit void within sight lines of the second lens and the slit piece defining a second slit void within sight lines of the third lens; and
   d) a home sensor.

7. A method to measure refraction errors of a user using an optical device and a personal electronic device, the method comprising the steps of:
   a) positioning the optical device over a screen of the personal electronic device;
   b) using the screen of the personal electronic device to depict a first and second image;
   c) disposing lenses within the optical device wherein the lenses are between the screen of the personal electronic device and a user, the lenses comprising a first lens of demagnification, a colored second lens and a colored third lens;
   d) using a slit piece defining a first slit void aligned to the second lens and the slit piece defining a second slit void aligned to the third lens;
   e) using the user control system to align, based upon the perception of the user, the first and the second image depicted upon the screen of the personal electronic device to define a user generated position of alignment;
   f) using the user generated position of alignment to derive a refraction error correction for the user.

8. The method of claim 7 further including the step of rotating the first and second image depicted upon the display screen and using a motor and user control system to enable a user to rotate the slit piece, second lens and third lens to perform the alignment procedure for different meridians of images and positions to obtain additional refraction error data of the user based upon the user generated position of alignment obtained from the user.

* * * * *